(12) United States Patent
Myrman (10) Patent No.: US 7,278,426 B2
(45) Date of Patent: Oct. 9, 2007

(54) SECURING DOSE QUALITY OF AN INHALABLE DRUG

(75) Inventor: Mattias Myrman, Tyreso (SE)

(73) Assignee: Mederio AG, Hergiswil NW (CH)

( * ) Notice: Subject to any disclaimer, the term of this patent is extended or adjusted under 35 U.S.C. 154(b) by 0 days.

(21) Appl. No.: 11/144,832

(22) Filed: Jun. 6, 2005

(65) Prior Publication Data

US 2006/0000473 A1    Jan. 5, 2006

(30) Foreign Application Priority Data

Jun. 7, 2004    (SE) .................................. 0401453-6

(51) Int. Cl.
*A61M 15/00* (2006.01)

(52) U.S. Cl. .............................. 128/203.15; 128/200.12

(58) Field of Classification Search ........... 128/200.12, 128/200.18, 200.22, 200.23, 203.15, 203.18, 128/203.19, 203.21

See application file for complete search history.

(56) References Cited

U.S. PATENT DOCUMENTS

| | | | |
|---|---|---|---|
| 5,415,162 A | | 5/1995 | Casper et al. |
| 5,595,175 A | | 1/1997 | Malcher et al. |
| 6,422,236 B1 | * | 7/2002 | Nilsson et al. ......... 128/203.15 |
| 6,698,425 B1 | | 3/2004 | Widerstroem |
| 6,722,363 B1 | * | 4/2004 | Von Schuckmann ... 128/203.15 |
| 2003/0164169 A1 | * | 9/2003 | Stangl et al. .......... 128/203.12 |
| 2004/0118399 A1 | * | 6/2004 | Young et al. .......... 128/203.15 |
| 2005/0028813 A1 | * | 2/2005 | Harrison ................ 128/200.22 |
| 2006/0060194 A1 | * | 3/2006 | Oliva .................... 128/203.15 |

FOREIGN PATENT DOCUMENTS

| | | |
|---|---|---|
| EP | 0 490 797 A1 | 6/1992 |
| EP | 0 759 306 A2 | 2/1997 |

OTHER PUBLICATIONS

U.S. Appl. No. 11/144,832, filed Jun. 6, 2005, Myrman.
U.S. Appl. No. 11/144,941, filed Jun. 6, 2005, Myrman.

\* cited by examiner

*Primary Examiner*—Steven O. Douglas
(74) *Attorney, Agent, or Firm*—Oblon, Spivak, McClelland, Maier & Neustadt, P.C.

(57) ABSTRACT

A method and a device for making a metered dry powder medication dose, enclosed in a dose container, accessible for inhalation with a minimum of exposure to ambient atmosphere.

16 Claims, 5 Drawing Sheets

SECURING DOSE QUALITY OF AN INHALABLE DRUG

REFERENCE TO PRIOR APPLICATIONS

This application claims priority to Swedish patent application SE0401453-6 filed Jun. 7, 2004, incorporated herein by reference.

TECHNICAL FIELD

The present invention relates to securing the dose quality of an inhalable drug, including a method and a device applied in a dry powder inhaler for bringing a medicament dose into the dry powder inhaler in advance of an inhalation. Among other things, a method of making a metered dry powder medication dose, enclosed in a dose container, accessible for inhalation with a minimum of exposure to ambient atmosphere and a hand-operated device for carrying out the method are disclosed.

BACKGROUND

Within health care today administration of medicaments by inhalation for distributing dry powder medicaments directly to the airways and lungs of a user is becoming more and more popular, because it offers an efficient, fast, and user friendly delivery of the specific medication substance.

Different types of inhalers are available on the market today, such as metered dose inhalers (MDIs), nebulizers and dry powder inhalers (DPIs). MDIs use medicaments in liquid form and may use a pressurized drive gas to release a dose. Usually MDIs have a relatively low capacity for delivering an effective dose of the active substance in a single inhalation and many devices have problems with using a drive gas which is environmentally acceptable. Nebulizers are fairly big, non-portable devices. Dry powder inhalers have become more and more accepted in the medical service, because they deliver an effective dose in a single inhalation, they are reliable, often quite small in size and easy to operate for a user. Two types are common, multi-dose dry powder inhalers and single dose dry powder inhalers. Multi-dose devices have the advantage that a quantity of medicament powder, enough for a large number of doses, is stored inside the inhaler and a dose is metered from the store shortly before it is supposed to be inhaled. Single dose inhalers either require reloading after each administration or they may be loaded with a limited number of individually packaged doses, where each package is opened shortly before inhalation of the enclosed dose is supposed to take place.

Gelatin or plastic capsules and blisters made of aluminum or plastic, or laminates comprising aluminum and plastic foil are common prior art containers for metered single doses of dry powder medicaments. Typically, the user has to open the inhaler, insert at least one container into the inhaler, close it, push a button to force one or more sharp instrument(s) to penetrate a selected container, such that the dose may be accessed by streaming air when the user at leisure decides to inhale the dose. Besides a method of breaking the container open inside the inhaler and pouring out the dose in a chamber first, the most common method of opening the container is to punch one or more holes in the container itself or in a foil sealing the container. In the first case the powder is poured onto a surface inside the inhaler and made available for inhalation from there. In the second case the dose is aerosolized by inhalation air being forced through the container or the dose being shaken out of the container and immediately aerosolized by streaming air on the outside of the container.

New types of dry powder medicaments, not least for systemic treatment, have a rather short expiry date and they are generally quite sensitive to ambient conditions, especially moisture during storage and in use. Hence, the demands put on dose protection and inhaler devices in handling sensitive doses are therefore much higher than for prior art devices as used e.g. for administering traditional medicaments against respiratory disorders. For instance, prior art blister packages for dry powder medicaments, intended for inhaler use, often use a fairly thin polymeric seal, which can be easily ripped or punched open before the dose is supposed to be inhaled. Another common seal is a peelable blister such that the blister is peeled open prior to inhalation of the enclosed dose. Yet another type of prior art dose container is the capsule. Capsules are often made by gelatin, but polymers and cellulose and other materials are also used. A common problem for prior art blisters and capsules used for dry powder doses for inhalation is that the primary package does not protect sensitive substances from moisture well enough during storage and in use. Minimizing the time the primary package is exposed to the atmosphere and minimizing the time during which the dose is subjected to the ambient atmosphere after opening of the container are therefore important aspects of inhaler and dose container design.

There is a demand for an improved method and device, which will simplify loading and opening of the dose container to make the powder dose enclosed therein easily available to a user of the DPI.

SUMMARY

The present invention relates in one embodiment to a single dose inhaler, which is provided with a movable inhaler member, for example a so called slide, which has at least one matching receptacle adapted for receiving a selected type of dose container. Hereinafter, this member will be referred to as a slide for simplicity, but this is not the only embodiment of this member. The slide is preferably movable between a first, protruding position, where the receptacle(s) is accessible for loading of a sealed dose container by a user, and a second, retracted position inside the inhaler.

In a particular embodiment the slide carrying an unopened, sealed dose container is arranged to be pushed by a user's hand force from the first position to the second position. During the motion the seal of the dose container is opened by an opening member provided inside the inhaler. As the container continues into the inhaler by the pushing action the dose inside the container is accessed by an inhalation-induced flow element, e.g. directed by a suction nozzle being in close proximity to the dose as it, too, moves into the inhaler carried by the slide.

Optionally, the inhaler is provided with a breath-actuated latch mechanism preventing the slide from being pushed from the first position, if the receptacle is loaded with a dose container, unless a suction exceeding a certain minimum magnitude is provided by the user sucking at a mouthpiece of the inhaler. This breath-actuation helps the user to synchronize the pushing action with an act of inhalation.

In all instances where movement occurs herein between parts in the device and in the practice of the invention, any one, two or more parts may move so as to accomplish the intended function. Illustrated and discussed embodiments are for illustration only.

DESCRIPTION OF THE DRAWINGS

The invention will be described in the form of nonlimiting preferred and illustrative embodiments and by means of the attached drawings, wherein like reference numbers indicate like or corresponding elements and wherein.

DESCRIPTION OF AN ILLUSTRATIVE EMBODIMENT

The present invention relates to a method and a device for making a metered dry powder medication dose in a dose container accessible inside a dry powder inhaler (DPI) in direct connection with an inhalation of the enclosed dose.

Advantages brought by the invention include
Secures dose quality
Simple inhaler design
Few parts needed
Low cost
Small inhaler size
Ease of use
Safety
High level of user compliance
Titratable dosing by user possible, i.e. different dose sizes may be selected by user
All types of inhalable dry powder drugs may be used In a particular aspect of the present invention, the method comprises bringing a sealed container carrying a single medicament dose into the inhaler by means of a movable inhaler member, for example a so called slide as noted above. A user has access to the slide in a first, protruding position. The slide comprises at least one matching receptacle designed for a particular type of dose container. An advantage of the invention is that the user has access to the slide, but no access to the internal parts of the inhaler, whereby unintentional damage or contamination of sensitive parts is avoided. Pushing the slide inwards into the inhaler body, the motion ends in a second, retracted position. Pushing the slide is done preferably by hand or optionally by a motor. The dose container is thus brought into the inhaler. The user pushes the slide into the inhaler while at the same time inhaling through a mouthpiece of the inhaler. As the dose container enters the inhaler, the container seal begins to be opened up by an opener device integrated in the inhaler, thereby letting ambient air into the container and into the dose powder. But at the same time one or more flow elements of the inhaler gains access to the dose and a concurrent release of the dose into an inhalation air-stream begins. The time lapse between opening of the seal and dose release is extremely short, which secures the quality of the dose when delivered to the inhaling user. Typically, the time the particles of the dose are exposed to the atmosphere before they are entrained into inspiration air is only a split second. When the slide reaches a second, fully retracted position, the dose has already been delivered. Preferably, however, the slide cannot move from the first position unless a sufficiently strong inhalation is already in progress. Thus, the transport, container opening and dose delivery are carried out in a single user-initiated action. In this way, the dose is exposed to the atmosphere for a minimum time, in fact only for the duration of a complete dose delivery. The exposure of the dose to the atmosphere is consistently short every time and actually less than the inhalation time itself.

Figure 2A:
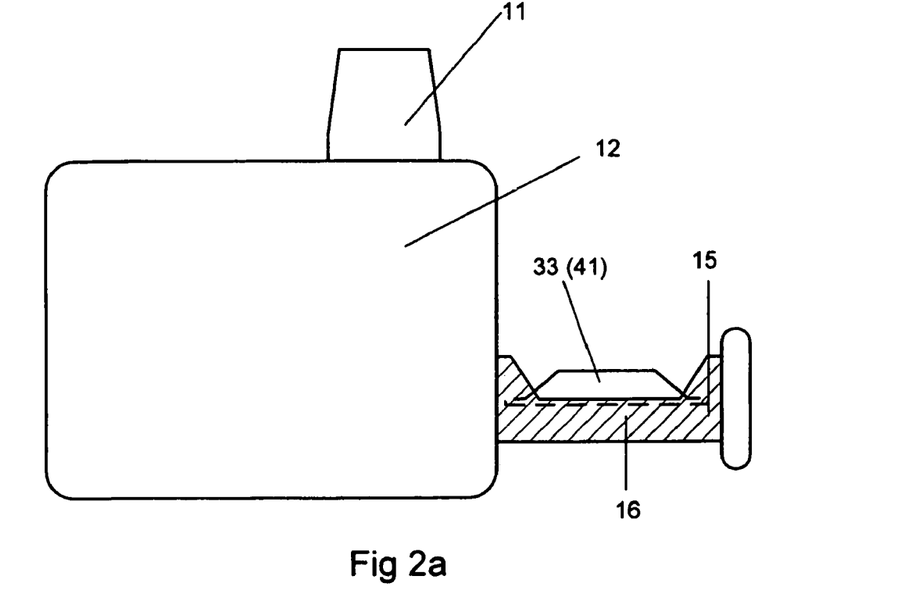
FIG. 2a-2c illustrates a slide applied in a single dose dry powder inhaler in a top view with slide in a protruding position (FIG. 2a) and slide in a retracted position (FIG. 2b) and a side view (FIG. 2c) of slide and inhaler.
Figure 2B:
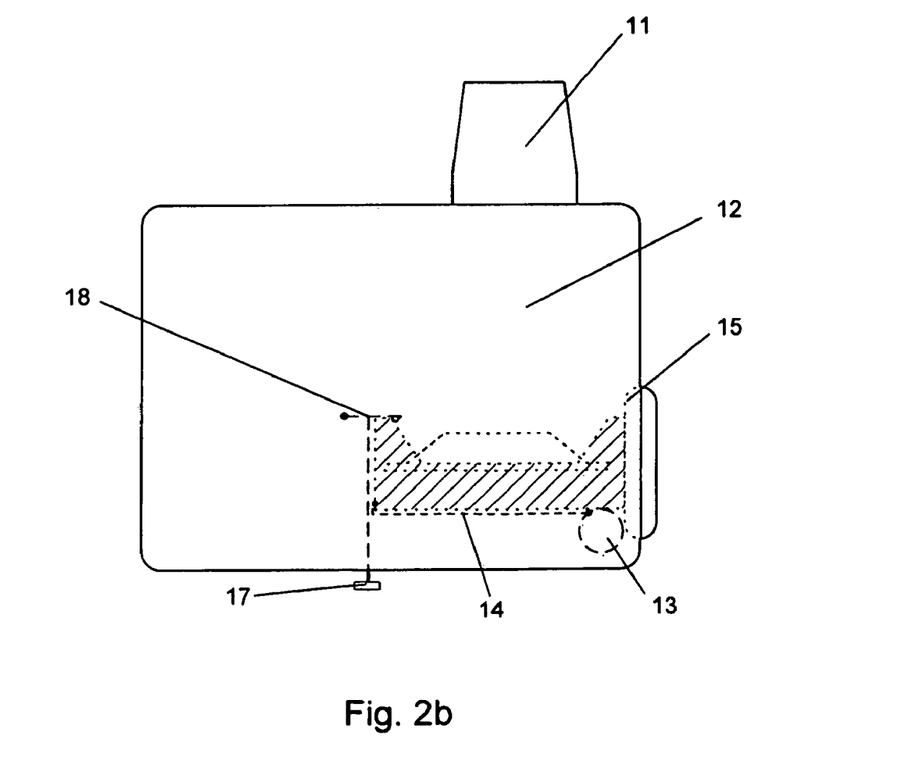
Figure 2C:
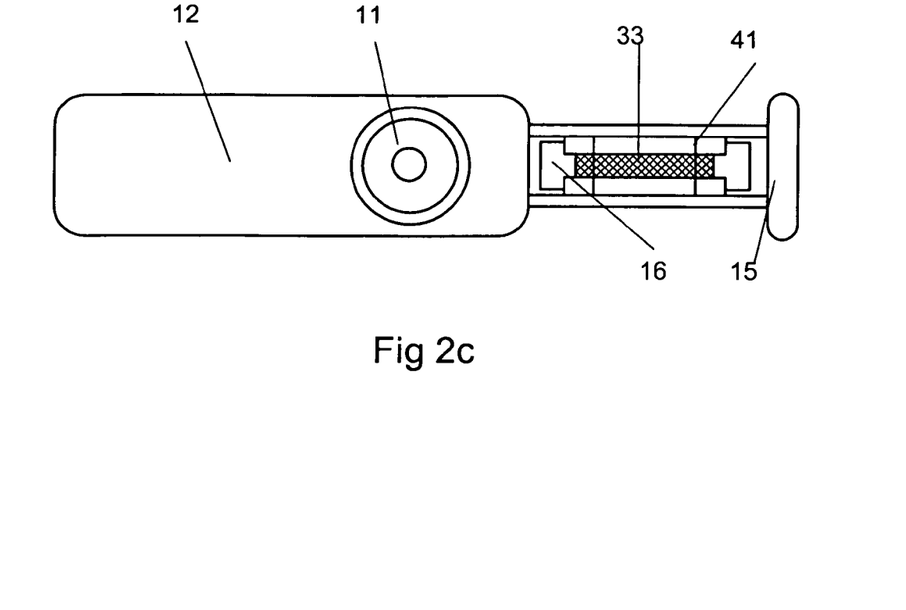

In a further aspect of the invention, illustrated in FIGS. 2a, 2b and 2c, the slide 15 is provided with at least one matching receptacle 16 for a selected type of single dose container 33 in a protective casing 41. Only the defined selected type of dose container 33+41 can be inserted into the receptacle. After the dose has been delivered the slide remains in the second, retracted position until the user activates the slide, such that it comes out of the inhaler 12 carrying the now spent empty container. The user removes the spent container 33+41 and discards it. Pushing the slide without container back into the inhaler closes the inhaler shut. The user may activate the slide as needed when the time comes for administering a new dose. Thus, the user needs never to have access to the inside of the inhaler. According to the present invention, this novel method of protecting a dose and bringing it into an inhaler 12, having a mouthpiece 11, makes it possible to arrange a very efficient, high quality dose delivery with negligible risk of dose degradation and of foreign matter being accidentally introduced into the inhaler by the user.

By relying on the user to provide the energy to move the slide and the inhalation effort for delivering the dose, a very simple, compact and robust inhaler design is possible. As a result the cost is low and the uncomplicated design makes the manufacturing simple and very little can go wrong with the inhaler in the hands of a user.

Figure 1:
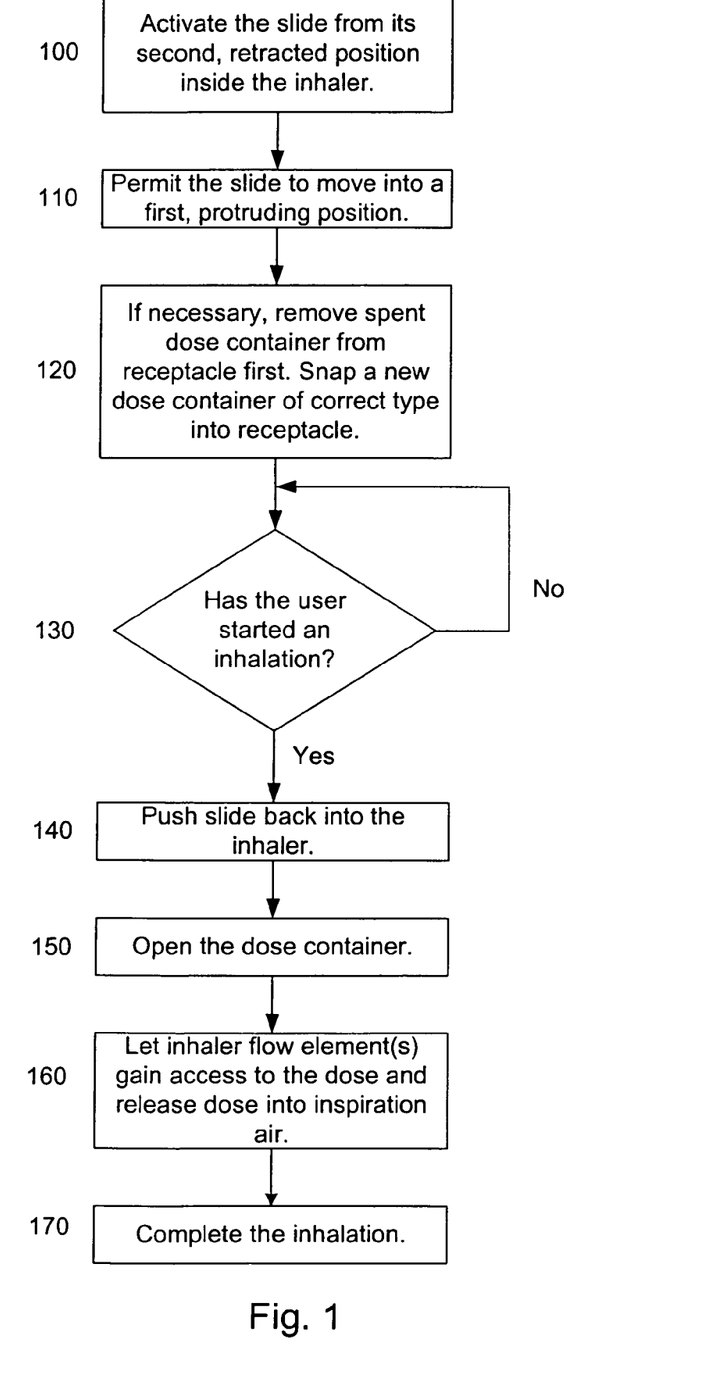
FIG. 1 illustrates in a flow diagram a particular method of the present invention.
Figure 5A:
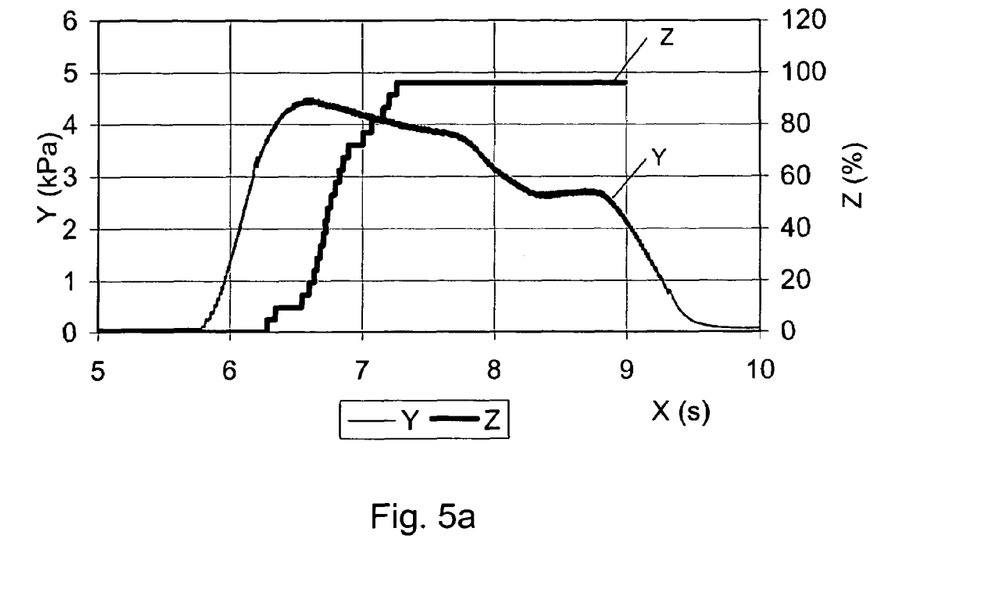
FIG. 5a-5b illustrates two typical inhalation sequences (FIG. 5a and FIG. 5b) when applying the present invention to a dry powder inhaler.
Figure 5B:
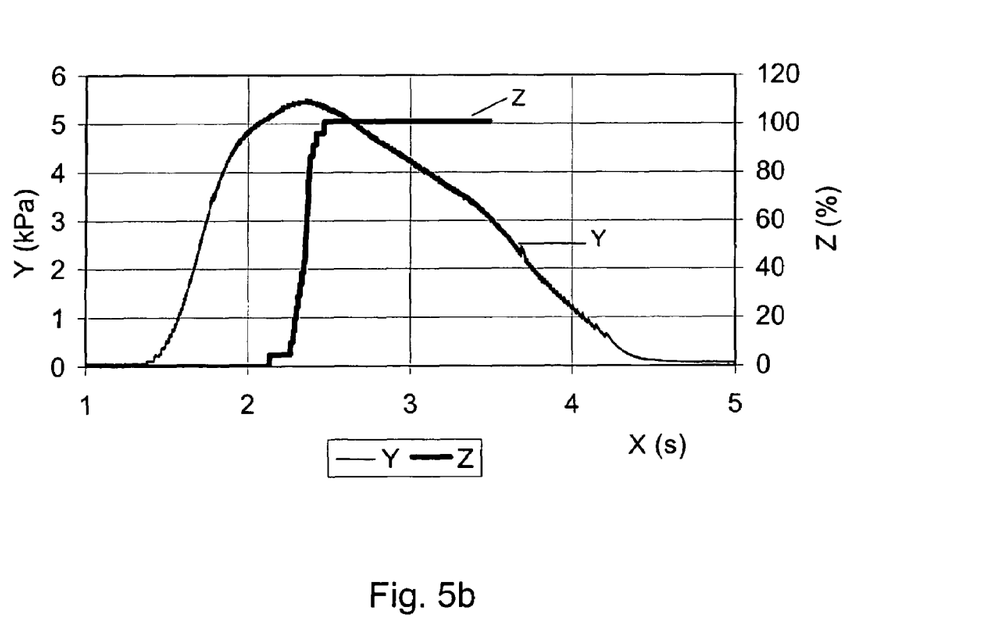

A particular method is described in a flow chart illustrated in FIG. 1. Reference is also made to FIGS. 2a to 2c. A movable inhaler member, constituting a slide 15, being in a normal, fully retracted position inside the inhaler body 12, is activated in an optional step 100 by e.g. a pushbutton accessible on the inhaler. Preferably, the slide 15 is held in the fully retracted position by a latch mechanism 18, so that it cannot move until the latch 18 is released by any suitable means, e.g. a spring loaded pushbutton 17. Preferably, when the slide 15 is released it will come out of the inhaler 12 automatically, i.e. without further assistance from a user, into a first, fully protruding, dose loading position, step 110, where the slide 15 is ready to accept at least one dose container 33. If the inhaler 12 has been used before, it is possible that a spent container is still held in at least one receptacle 16 in the slide 15 and must be removed before a new one can be fitted. A new, selected container 33 of the correct type may now be snapped into the matching receptacle 16, step 120. Preferably, the container 33 snaps into place and remains firmly held there, with no possibility of moving relative the slide 15. In a particular embodiment of the present invention, on condition that a user has started an inhalation, step 130, the slide 15 is now pushed inwards into the inhaler 12, step 140, bringing the container 33 with it. As the container 33 enters the inhaler body 12 it is opened, step 150, by suitable opening means and a stream of air is then directed to the dose by an adapted flow element, e.g. a suction nozzle, step 160. The particles of the dose are thereby released and entrained into the inspiration airflow leaving the mouthpiece 11, step 170. In a preferred embodiment of the present invention, the container 33 is opened while being transported into the inhaler 12. In an alternative embodiment the container 33 may be opened when the slide 15 reaches its second, fully retracted position, or proximate this position, inside the inhaler 12. See FIG. 5 which illustrates a typical opening of a container synchronized with an inhalation. Diagram curve Y represents the suction power in kPa provided by the user over time X and curve Z represents the container motion from 0 (starting position) to 100% (end position) in the DPI.

In a preferred embodiment according to the disclosure, however, it is advantageous that the bringing of the slide with a dose container into the inhaler is synchronized to a commenced inhalation, such that the time during which the dose is exposed to the ambient atmosphere is minimized. Obviously, the container must be opened before a stream of air can access the dose. Preferably, the container starts to be opened at a predetermined point along the stroke made by the slide. A stream of inspiration air is directed into the container as it is being opened, whereby the air-stream gains access to the enclosed dose.

The disclosed method is easily adapted to the particular type of dose container, which has been selected for insertion into a particular, adapted dry powder inhaler. For instance, the receptacle in the slide, firmly holding the dose container, should be adapted and matched to the container type. Naturally, the piercing or opening members and the flow elements inside the inhaler should also be adapted for the container type. Thus, the air flow resulting from an inhalation is directed by proper channeling into the dose container, preferably as soon as the container is being opened by the piercing or opening members of the inhaler, such that the stream of air may release the dose and bring the dose into the inspiration air of a user without unnecessary delay. As already pointed out, different types of dose containers may be selected and advantageously used in the present invention. Examples of containers are aluminum or plastic single dose blisters of varying size and design and also capsules of gelatin, cellulose or plastics. A person of ordinary skill in the art will know how to adapt the receptacle in the slide, the insertion of the dose container into the inhaler and the inhaler itself, including the piercing or cutting members and air flow channels, to a particular type of dose container, in view of this disclosure.

The disclosed method eliminates as far as possible any adverse influence that e.g. humidity in the air may have on the fine particles in the dose, such as creating particle aggregates and making aggregates more difficult to de-aggregate when sucked up and delivered to a user of the inhaler. Minimizing the dose exposure to the atmosphere may preferably be done by implementing a breath actuation mechanism in the inhaler. The breath actuation blocks the bringing of the slide and container into the inhaler until the user applies at least a minimum suction power to a mouthpiece of the inhaler. For instance, a pressure sensitive flap may be arranged to open when the applied suction is strong enough, thus letting air flow into the air channels of the inhaler, which are in fluid connection with the mouthpiece. When the flap opens, the blocking of the slide is removed and the slide may be pushed into the inhaler while the inhalation is in an early stage of progress.

In a further aspect, see FIG. 2*b*, of the present invention a damper mechanism 13 is attached to the slide 15. In a particular embodiment the damper device 13 provides a first counterforce counteracting the slide motion out of the inhaler body 12 after the slide 15 has been activated and released from its fully retracted position. The slide motion out of the inhaler 12 may optionally but preferably be governed and powered by a spring mechanism 14 that provides a spring force, which is reasonably constant. The spring-driven motion is balanced by the damper device 13 along the full stroke, or part thereof, of the slide 15 from a second, fully retracted position into a first, fully protruding position. The speed of the slide 15 coming out of the inhaler 12 is thus kept constant. The same or a different damper 13 may provide a second counterforce, which may or may not be of the same magnitude as the first counterforce, opposing an applied force pushing the slide 15 back into the inhaler body 12. The applied pushing force may be a manual force provided by a user of the inhaler 12, or it may be provided by an independent source of power, e.g. in a particular embodiment where the slide 15 is governed and powered by an electric motor device. The damper 13 acts to control the speed of the slide motion into the inhaler 12 by providing a suitable, second counterforce formed by the damper 13, such that the speed of the slide 15 into the inhaler 12 is kept reasonably constant.

Disregarding the cost aspect, a motorized drive system may replace the spring mechanism and optionally the dampers and/or the manual pushing force provided by a user. This version of moving the slide may e.g. be used where a user has physical handicaps, which restricts or excludes manual use of the device. As a person skilled in the art will realize, the driving force, necessary for driving the relative motion of the slide in and out of the inhaler, may come from any type of power source, e.g. electric, hydraulic, pneumatic, spring, mechanical or manual by a user. However, hand operation by a user is normally preferred, because it offers a low cost, simple and safe administration of any type of inhalable dry powder drug.

In another embodiment, however, when a dose container is selected, which is not suitable for concurrent transport, opening and dose delivery, the disclosed method and device may be adjusted to comprise the bringing of the container into a position in the inhaler where the container may be kept in an unopened state prepared for later delivery. Preferably, a movable inhaler member, e.g. a slide, is used for bringing the container into this position and keeping it there, until the container is opened by suitable means incorporated in the inhaler, e.g. an opener or one or more sharp, piercing instrument. Preferably, opening is triggered by an act of inhalation, such that the enclosed dose may be entrained into inspiration air directly from the container as soon as the container has been opened. In this case too, the user has no access to the internals of the inhaler. However, such alternative embodiments might prevent that a gradual and optionally prolonged release of the dose is obtained. This is an important feature obtained in the preferred embodiment. A corresponding function of another embodiment, where the slide with the dose container is resting inside the device before commencing an inhalation, will make this embodiment more complicated leading to a more expensive design of the particular adapted inhaler.

In another aspect of the present invention, the time between opening of a selected dose container and inhalation of the enclosed dose is on the order of a split second, which is so short that it is negligible. Prior art inhalers allow much longer times between subjecting the selected dose to the ambient atmosphere and an actual inhalation of the dose taking place. Some prior art inhalers have no control over time lapse between breaking the dose container open and a following inhalation. In any case, by the influence of the ambient atmosphere and especially moisture, the dose may decompose rapidly, such that when the user finally gets round to inhaling the dose, it may have deteriorated seriously. The user will then unknowingly get a smaller therapeutic effect than intended.

Figure 3:
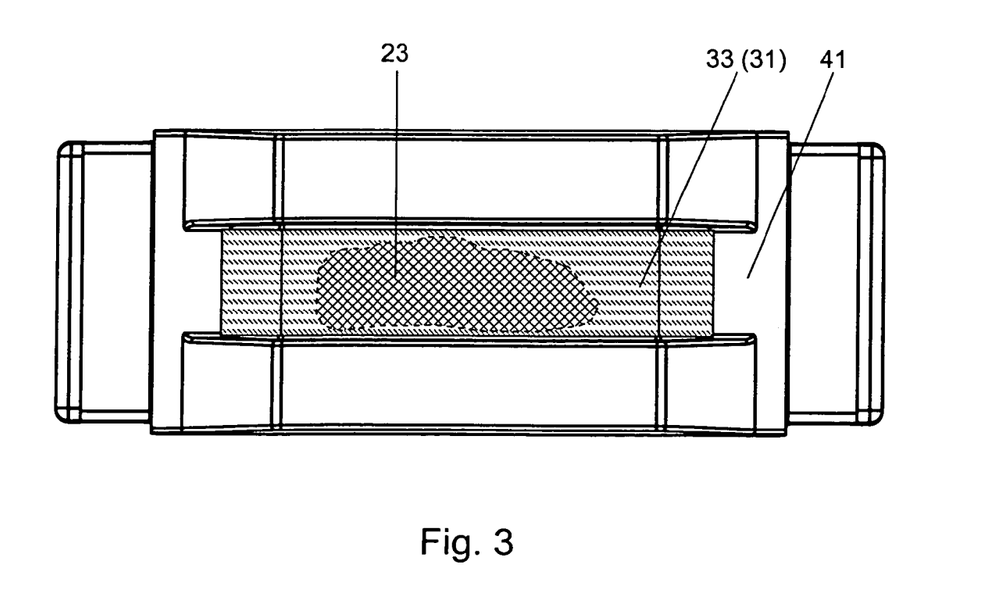
FIG. 3 illustrates a sealed dose container carrying an enclosed dose adapted for the slide in FIG. 2.
Figure 4A:
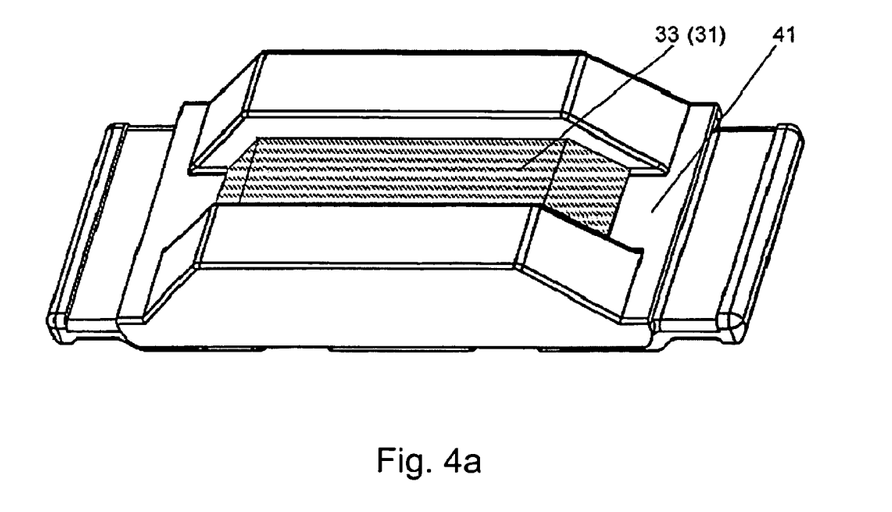
FIG. 4a-4c illustrates in perspective (FIG. 4a), top (FIG. 4b) and front (FIG. 4c) views a particular embodiment of a sealed dose container, adapted for the present invention.
Figure 4B:
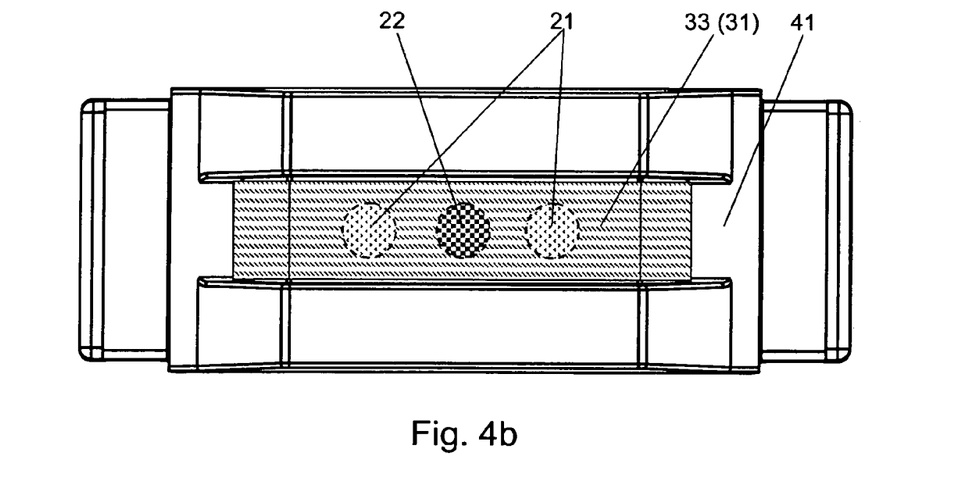
Figure 4C:
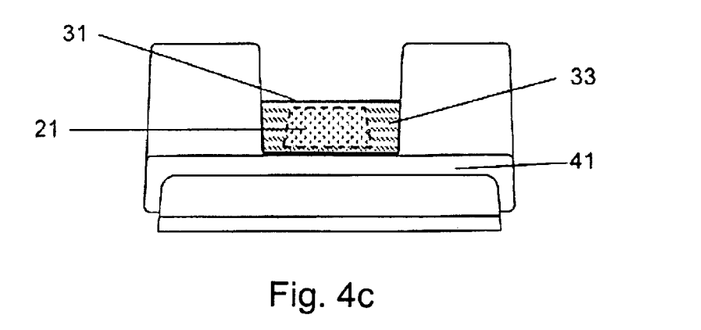

Naturally, using a new type of blister pack, a so-called pod, as a particular embodiment of a sealed dose container, is to be preferred in an application where the present invention is to be put to use. See FIG. 3 illustrating a sealed dose container 33 in a protective casing 41. The container encloses a dose 23, illustrated for the benefit of the reader, although the dose is located under a seal 31. Containers providing high quality high barrier seals, such as a pod, are particularly suited for use of the present invention. High barrier seals require a pushing force of considerable strength to power opening of the seal. The hand operated slide provides ample power to overcome resistance from the sealing, as opposed to many prior art inhalers. See FIG. 4 illustrating a pod carrying a sealed container in a perspective drawing. FIG. 4a shows a sealed container 33 (seal 31) put into a protective casing 41 adapted for insertion into a dry powder inhaler. FIG. 4b shows a top view of the carrier/container and indicates depositions 21, 22 of dry powder making up a metered dose inside the container 33 under a seal 31, for the benefit of the reader. FIG. 4c illustrates a front view of the carrier/container in FIG. 4b.

However, the present invention may also advantageously be applied to conventional blister packs and capsules. Preferably, a person skilled in the art may use this disclosure by adapting e.g. when the container seal is to be opened during the course of moving the container from a starting position to an end position and adapting how it is opened to the particular type of container that is selected for use. Such adaptation is still within the scope of the present invention. An objective of the present invention is to make the time between opening of the container and delivery of the dose inside as short as possible and to make it impossible for the user to open the container without commencing an inhalation. If an inhalation is broken off prematurely for any reason, then the user will at least be aware that a full dosage may not have been delivered.

In cases where the medicament dosage is controlled by the user, a single dose dry powder inhaler is preferred, because the user may then select a dosage among pre-metered doses, which is well adjusted to the situation and condition the user is in.

It will be understood by those skilled in the art that various modifications and changes may be made to the present invention without departing from the scope thereof, which is defined by the appended claims.

As used herein, the phrases "selected from the group consisting of," "chosen from," and the like include mixtures of the specified materials.

All references, patents, applications, tests, standards, documents, publications, brochures, texts, articles, instructions, etc. mentioned herein are incorporated herein by reference. Where a numerical limit or range is stated, the endpoints are included. Also, all values and sub-ranges within a numerical limit or range are specifically included as if explicitly written out.

The above written description of the invention provides a manner and process of making and using it such that any person skilled in this art is enabled to make and use the same, this enablement being provided in particular for the subject matter of the appended claims, which make up a part of the original description and including a method of reducing time of exposure of a medical dry powder dose enclosed in a sealed dose container to ambient atmosphere in connection with an inhalation of said dose using a single dose dry powder inhaler, comprising the steps of snapping the dose container into a matching receptacle of a movable inhaler member, a slide, being in a first, protruding position;

synchronizing an act of inhalation and a pushing of the slide back into the inhaler from the first position of slide into a second, retracted position;

bringing the dose container gradually inside the inhaler by the slide motion where the dose container seal is opened up during the motion and one or more inhaler flow elements are concurrently accessing and releasing the dose before the slide has reached the second position, whereby the time lapse between opening of seal and dose release, i.e. exposure to ambient atmosphere, is extremely short.

What has been said in the foregoing is by example only and many variations to the disclosed embodiments may be obvious to a person of ordinary skill in the art, without departing from the spirit and scope of the invention as defined in the appended claims.

I claim:

1. A method of reducing time of exposure of a medical dry powder dose enclosed in a sealed dose container to ambient atmosphere in connection with an inhalation of said dose using a single dose dry powder inhaler, comprising:
   snapping the dose container into a matching receptacle of a moveable inhaler member, a slide, being in a first, protruding position;
   synchronizing an act of inhalation and a pushing of the slide back into the inhaler from the first position of slide into a second, retracted position;
   wherein said pushing of the slide back into the inhaler brings the dose container gradually inside the inhaler by the slide motion and wherein the sealed dose container is opened during the motion and one or more inhaler flow elements concurrently access and release the dose before the slide has reached the second position.

2. The method according to claim 1, wherein the slide is moved from the first position into the second position in less than 5 s.

3. The method according to claim 1, wherein the slide is moved from the first position into the second position in less than 2 s.

4. The method according to claim 1, further comprising restricting the motion of the moveable inhaler member with a breath-actuation mechanism, which requires suction to be applied to a mouthpiece of the inhaler whereby a certain minimum suction pressure has to be exceeded before the motion of the moveable inhaler member can begin.

5. The method according to claim 1, said inhaler further comprising a spring to power the motion of the slide out of the inhaler body from the second position into the first position.

6. The method according to claim 1, further comprising adjusting the speed of the moveable member, such that the time for pushing the moveable member from the first position to the second position is not less than 0.2 s and not more than 2 s.

7. The method according to claim 1, further comprising opening the dose container when the moveable member is in the second retracted position or in close proximity to the second retracted position.

8. The method according to claim 1, wherein the motion of the slide is in a straight line only.

9. A method of reducing time of exposure of a medical dry powder dose enclosed in a sealed dose container to ambient atmosphere in connection with an inhalation of said dose using a single dose dry powder inhaler, comprising:
   snapping the dose container into a matching receptacle of a moveable inhaler member, a slide, being in a first, protruding position;
   releasably locking the dose container in its matching receptacle, such that it cannot move relative the slide;
   synchronizing an act of inhalation and a pushing of the slide back into the inhaler from the first position of slide into a second, retracted position;
   wherein said pushing of the slide back into the inhaler brings the dose container gradually inside the inhaler by the slide motion and wherein the sealed dose container is opened during the motion and one or more inhaler flow elements concurrently access and release the dose before the slide has reached the second position.

10. A method of reducing time of exposure of a medical dry powder dose enclosed in a sealed dose container to ambient atmosphere in connection with an inhalation of said dose using a single dose dry powder inhaler, comprising:
   snapping the dose container into a matching receptacle of a moveable inhaler member, a slide, being in a first, protruding position;
   synchronizing an act of inhalation and a pushing of the slide back into the inhaler from the first position of slide into a second, retracted position, wherein said pushing of the slide back into the inhaler brings the dose container gradually inside the inhaler by the slide motion and wherein the sealed dose container is opened during the motion and one or more inhaler flow elements concurrently access and release the dose before the slide has reached the second position;
   activating the slide when in the second, retracted position inside the inhaler body, whereby the slide is released and permitted to extend out of the inhaler body into the first, protruding position, the motion out of the inhaler optionally not requiring assistance by a user.

11. A method of reducing time of exposure of a medical dry powder dose enclosed in a sealed dose container to ambient atmosphere in connection with an inhalation of said dose using a single dose dry powder inhaler, comprising;
   snapping the dose container into a matching receptacle of a moveable inhaler member, a slide, being in a first, protruding position;
   synchronizing an act of inhalation and a pushing of the slide back into the inhaler from the first position of slide into a second, retracted position;
   providing a resisting motion of the slide from the first position to the second position by applying a controlled counterforce balancing the pushing force, such that the speed of the motion is kept generally constant from the first to the second position,
   wherein said pushing of the slide back into the inhaler brings the dose container gradually inside the inhaler by the slide motion and wherein the sealed dose container is opened during the motion and one or more inhaler flow elements concurrently access and release the dose before the slide has reached the second position.

12. A slide device for bringing an exchangeable dose container harbouring an enclosed, metered, dry powder medication dose into a single dose dry powder inhaler for securing quality of the delivered medication dose, wherein
   the slide device constitutes a user-operated member of the inhaler, reversibly moveable between a first, protruding position and a second, retracted position in the inhaler, the slide device comprising:
   at least one matching receptacle for a dose container;
   a brake limiting the speed of the slide motion from the first to the second position; and
   a release for releasing the slide device from a latched condition in the second, retracted position.

13. The slide device according to claim 12, wherein
   the slide device comprises a latch for preventing the motion of the slide device from the first position into the inhaler, the latch is connected to a breath-actuation mechanism of the inhaler, the breath-actuation mechanism requiring a certain minimum suction pressure to be exceeded by a user applying a suction to a mouthpiece of the inhaler, before releasing the latch such that motion of the slide device can begin.

14. The slide device according to claim 13, further comprising a damper unit as a brake, presenting a controlled counterforce balancing a pushing force by the driving spring, such that the speed of the motion is generally constant.

15. The slide device according to claim 12, further comprising a driving spring is arranged for driving the slide from the second, retracted position out of the inhaler body into a first, protruding position, the spring is optionally combined with a brake to limit the speed of motion.

16. The slide device according to claim 12, wherein the motion of the slide device is in a straight line only.

* * * * *